(12) United States Patent
He et al.

(10) Patent No.: US 7,083,162 B2
(45) Date of Patent: Aug. 1, 2006

(54) INTERMEDIARY DEVICE

(75) Inventors: Mengtao Pete He, Scottsdale, AZ (US); David Rinaldis, Longmont, CO (US); Christopher Cowart, Boulder, CO (US); Ralf Groene, Boulder, CO (US); Debra Park, Mesa, AZ (US); Kristopher Stathakis, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 161 days.

(21) Appl. No.: 10/653,649

(22) Filed: Sep. 2, 2003

(65) Prior Publication Data

US 2004/0113294 A1 Jun. 17, 2004

Related U.S. Application Data

(60) Provisional application No. 60/407,394, filed on Aug. 30, 2002.

(51) Int. Cl.
*B01F 3/04* (2006.01)

(52) U.S. Cl. .............. 261/142; 261/DIG. 88; 261/DIG. 89; 239/53; 422/125

(58) Field of Classification Search ............. 261/142, 261/DIG. 88, DIG. 89; 239/53, 57; 219/473; 362/226, 253; 422/125, 124
See application file for complete search history.

(56) References Cited

U.S. PATENT DOCUMENTS

| | | | |
|---|---|---|---|
| 1,836,600 A | 12/1931 | Jones | |
| 2,539,696 A * | 1/1951 | Morrison | 422/125 |
| 3,262,290 A | 7/1966 | Huber | |
| 3,748,438 A | 7/1973 | Costello | |
| 3,780,260 A | 12/1973 | Eisner | |
| 3,895,928 A | 7/1975 | Gonzalo | |
| 3,908,905 A | 9/1975 | Von Philipp et al. | |
| 3,923,458 A | 12/1975 | Gonzalo | |
| 3,948,445 A | 4/1976 | Andeweg | |
| 4,017,030 A | 4/1977 | Coplan et al. | |
| 4,037,353 A | 7/1977 | Hennart et al. | |
| 4,084,079 A | 4/1978 | Costello | |
| 4,111,655 A | 9/1978 | Quincey | |
| 4,123,741 A | 10/1978 | Kiyono et al. | |
| 4,165,835 A | 8/1979 | Dearling | |
| 4,171,340 A | 10/1979 | Nishimura et al. | |
| 4,208,012 A | 6/1980 | Dutcher | |
| 4,214,146 A | 7/1980 | Schimanski | |
| 4,220,281 A | 9/1980 | Martens, III et al. | |
| 4,228,124 A | 10/1980 | Kashihara et al. | |
| 4,242,969 A | 1/1981 | Steigerwald et al. | |
| 4,293,173 A | 10/1981 | Tricca | |

(Continued)

FOREIGN PATENT DOCUMENTS

DE 35 35 564 5/1986

(Continued)

OTHER PUBLICATIONS

PCT International Search Report issued Dec. 17, 2003 for International Application No. PCT/US03/26511, International Filing Date Aug. 26, 2003, 4 pages.

(Continued)

*Primary Examiner*—Robert A. Hopkins
(74) *Attorney, Agent, or Firm*—Snell & Wilmer LLP

(57) ABSTRACT

The present invention provides an intermediary device which alters a surrounding environment and attaches to and/or integrates with at least one other device with little or no effect on devices to which the intermediary device is attached.

5 Claims, 6 Drawing Sheets

U.S. PATENT DOCUMENTS

| | | |
|---|---|---|
| 4,294,778 A | 10/1981 | DeLuca |
| 4,346,059 A | 8/1982 | Spector |
| 4,391,781 A | 7/1983 | Van Lit |
| 4,408,813 A | 10/1983 | Koehler |
| 4,413,779 A | 11/1983 | Santini |
| 4,415,797 A | 11/1983 | Choustoulakis |
| 4,425,302 A | 1/1984 | Pons Pons |
| 4,467,117 A | 8/1984 | Zobele |
| 4,518,212 A | 5/1985 | Rumble |
| 4,530,556 A | 7/1985 | Bonus |
| 4,537,351 A | 8/1985 | Wilson |
| 4,544,592 A | 10/1985 | Spector |
| 4,549,250 A | 10/1985 | Spector |
| 4,556,539 A | 12/1985 | Spector |
| 4,571,485 A | 2/1986 | Spector |
| 4,574,181 A | 3/1986 | Spector |
| 4,595,564 A | 6/1986 | Spector et al. |
| 4,631,387 A | 12/1986 | Glucksman |
| 4,658,985 A | 4/1987 | Madsen et al. |
| 4,660,764 A | 4/1987 | Joyaux et al. |
| 4,662,679 A | 5/1987 | Franck et al. |
| 4,675,504 A | 6/1987 | Suhajda |
| 4,686,353 A | 8/1987 | Spector |
| 4,695,434 A | 9/1987 | Spector |
| 4,703,155 A | 10/1987 | Suhajda |
| 4,707,336 A | 11/1987 | Jones |
| 4,714,984 A | 12/1987 | Spector |
| 4,718,856 A | 1/1988 | Pinkerton et al. |
| 4,725,712 A | 2/1988 | Schroeder |
| 4,731,520 A | 3/1988 | Glucksman |
| 4,731,522 A | 3/1988 | Manchester |
| 4,732,321 A | 3/1988 | Dolan |
| 4,734,560 A | 3/1988 | Bowen |
| 4,739,928 A | 4/1988 | O'Neil |
| 4,743,406 A | 5/1988 | Steiner et al. |
| 4,753,389 A | 6/1988 | Davis |
| 4,777,345 A | 10/1988 | Manchester |
| 4,780,286 A | 10/1988 | Parent et al. |
| 4,795,883 A | 1/1989 | Glucksman et al. |
| 4,798,935 A | 1/1989 | Pezaris |
| 4,800,239 A | 1/1989 | Hill |
| 4,801,271 A | 1/1989 | Piper |
| 4,804,821 A | 2/1989 | Glucksman |
| 4,808,347 A | 2/1989 | Dawn |
| 4,816,973 A | 3/1989 | Atalla et al. |
| 4,830,791 A | 5/1989 | Muderlak et al. |
| 4,837,421 A | 6/1989 | Luthy |
| 4,849,606 A | 7/1989 | Martens, III et al. |
| 4,853,517 A | 8/1989 | Bowen et al. |
| 4,878,615 A | 11/1989 | Losi |
| 4,886,469 A | 12/1989 | Jseng |
| 4,915,301 A | 4/1990 | Munteanu |
| 4,919,981 A | 4/1990 | Levey et al. |
| 4,931,224 A | 6/1990 | Holzner, Sr. |
| 4,931,258 A | 6/1990 | Zlotnik et al. |
| 4,968,456 A | 11/1990 | Muderlak et al. |
| D315,789 S | 3/1991 | Muderlak |
| 4,998,671 A | 3/1991 | Leifheit |
| 5,004,435 A | 4/1991 | Jammet |
| 5,014,913 A | 5/1991 | Hoyt et al. |
| 5,015,442 A | 5/1991 | Hirai |
| 5,029,729 A | 7/1991 | Madsen et al. |
| 5,038,394 A | 8/1991 | Hasegawa et al. |
| 5,050,798 A | 9/1991 | Sullivan |
| 5,106,317 A | 4/1992 | Taylor |
| 5,111,477 A | 5/1992 | Muderlak et al. |
| 5,115,975 A | 5/1992 | Shilling |
| 5,121,881 A | 6/1992 | Lembeck |
| 5,126,078 A | 6/1992 | Steiner et al. |
| 5,136,684 A | 8/1992 | Lonker et al. |
| 5,147,582 A | 9/1992 | Holzner, Sr. et al. |
| 5,148,984 A | 9/1992 | Bryson, Jr. et al. |
| 5,175,791 A | 12/1992 | Muderlak et al. |
| 5,196,171 A | 3/1993 | Peltier |
| 5,201,025 A | 4/1993 | Landesberg |
| 5,217,696 A | 6/1993 | Wolverton et al. |
| 5,220,636 A | 6/1993 | Chang |
| 5,222,186 A | 6/1993 | Schimanski et al. |
| 5,223,182 A | 6/1993 | Steiner et al. |
| 5,233,680 A | 8/1993 | Fussell |
| 5,239,610 A | 8/1993 | Shao |
| 5,240,426 A | 8/1993 | Barla |
| 5,285,014 A | 2/1994 | Gilchrist |
| 5,290,546 A | 3/1994 | Hasegawa et al. |
| 5,295,845 A | 3/1994 | Changxing |
| 5,309,338 A * | 5/1994 | Liu .......................... 362/253 |
| 5,314,669 A | 5/1994 | Hamilton |
| 5,320,542 A | 6/1994 | Cheng |
| 5,339,065 A | 8/1994 | Slenker |
| 5,342,584 A | 8/1994 | Fritz et al. |
| 5,373,581 A | 12/1994 | Smith |
| 5,375,728 A | 12/1994 | West |
| 5,376,338 A | 12/1994 | Zlotnik |
| 5,382,410 A | 1/1995 | Peltier |
| D355,251 S | 2/1995 | Paulovich et al. |
| 5,394,506 A | 2/1995 | Stein et al. |
| 5,402,517 A | 3/1995 | Gillett et al. |
| D357,330 S | 4/1995 | Wong et al. |
| 5,431,859 A | 7/1995 | Tobin |
| 5,431,885 A | 7/1995 | Zlotnik et al. |
| 5,445,802 A | 8/1995 | Wendelken |
| 5,465,198 A | 11/1995 | Kellogg |
| 5,480,591 A | 1/1996 | Lagneaux et al. |
| 5,481,442 A | 1/1996 | Wiltshire et al. |
| 5,484,086 A | 1/1996 | Pu |
| 5,498,397 A | 3/1996 | Horng |
| 5,521,357 A | 5/1996 | Lock et al. |
| 5,522,008 A | 5/1996 | Bernard |
| 5,547,616 A | 8/1996 | Dancs et al. |
| 5,556,192 A | 9/1996 | Wang |
| 5,567,361 A | 10/1996 | Harper |
| 5,574,821 A | 11/1996 | Babasade |
| 5,575,992 A | 11/1996 | Kunze |
| 5,577,156 A | 11/1996 | Costello |
| 5,591,395 A | 1/1997 | Schroeder et al. |
| 5,624,230 A | 4/1997 | Taylor et al. |
| 5,634,806 A | 6/1997 | Hahn |
| 5,647,052 A | 7/1997 | Patel et al. |
| 5,647,053 A | 7/1997 | Schroeder et al. |
| 5,651,942 A | 7/1997 | Christensen |
| 5,662,835 A | 9/1997 | Collingwood |
| 5,664,958 A | 9/1997 | Chadwick et al. |
| 5,700,430 A | 12/1997 | Bonnema et al. |
| 5,735,460 A | 4/1998 | Eisenbraun |
| 5,749,520 A | 5/1998 | Martin et al. |
| 5,750,498 A | 5/1998 | Soeda et al. |
| 5,765,751 A | 6/1998 | Joshi |
| 5,788,155 A | 8/1998 | Martin et al. |
| 5,788,931 A | 8/1998 | Munoz Quintana |
| 5,796,914 A | 8/1998 | Gatzemeyer et al. |
| 5,805,768 A | 9/1998 | Schwartz et al. |
| 5,810,265 A | 9/1998 | Cornelius et al. |
| 5,813,873 A | 9/1998 | McBain et al. |
| 5,832,648 A | 11/1998 | Malone |
| 5,873,529 A | 2/1999 | Johnson |
| 5,875,968 A | 3/1999 | Miller et al. |
| 5,884,808 A | 3/1999 | Muderlak et al. |
| 5,899,381 A | 5/1999 | Gordon et al. |
| 5,903,710 A | 5/1999 | Wefler et al. |
| 5,926,614 A | 7/1999 | Steinel |
| 5,928,605 A | 7/1999 | Bonnema et al. |
| 5,932,204 A | 8/1999 | Joshi |
| 5,937,140 A | 8/1999 | Leonard et al. |
| 5,940,577 A | 8/1999 | Steinel |

| | | | |
|---|---|---|---|
| 5,944,223 A | 8/1999 | Klima et al. | |
| 5,945,094 A | 8/1999 | Martin et al. | |
| 5,955,701 A | 9/1999 | Schockner et al. | |
| 5,957,701 A | 9/1999 | McMillin | |
| 5,970,643 A | 10/1999 | Gawel, Jr. | |
| 5,976,503 A | 11/1999 | Martin et al. | |
| 5,998,735 A | 12/1999 | Patterson, Jr. | |
| 6,021,254 A | 2/2000 | Hunter | |
| 6,031,967 A | 2/2000 | Flashinski et al. | |
| 6,032,930 A | 3/2000 | Calino | |
| 6,035,098 A * | 3/2000 | Chipalkatti et al. | 392/393 |
| 6,036,536 A | 3/2000 | Chiu | |
| 6,044,202 A | 3/2000 | Junkel | |
| 6,045,374 A | 4/2000 | Candeloro | |
| 6,050,551 A | 4/2000 | Anderson | |
| 6,051,788 A | 4/2000 | Nichols | |
| 6,078,728 A | 6/2000 | O'Rourke et al. | |
| 6,085,026 A | 7/2000 | Hammons et al. | |
| 6,097,881 A | 8/2000 | DeWitt et al. | |
| 6,099,137 A | 8/2000 | McCormick et al. | |
| 6,101,315 A | 8/2000 | Steinel, Jr. | |
| 6,104,866 A | 8/2000 | DeWitt et al. | |
| 6,104,867 A | 8/2000 | Stathakis et al. | |
| D430,659 S | 9/2000 | Zaraboza et al. | |
| 6,123,935 A | 9/2000 | Wefler et al. | |
| 6,141,496 A | 10/2000 | Sundberg et al. | |
| 6,148,143 A | 11/2000 | Steinel, Jr. | |
| 6,156,088 A | 12/2000 | Cardarelli | |
| 6,197,262 B1 | 3/2001 | Del Ben | |
| 6,197,263 B1 | 3/2001 | Blount | |
| 6,227,118 B1 | 5/2001 | Nance | |
| 6,236,807 B1 | 5/2001 | Ruffolo et al. | |
| 6,249,645 B1 | 6/2001 | Smith | |
| 6,254,065 B1 | 7/2001 | Ehrensperger et al. | |
| 6,264,548 B1 | 7/2001 | Payne, Jr. et al. | |
| 6,269,979 B1 | 8/2001 | Dumont | |
| 6,270,720 B1 | 8/2001 | Mandish | |
| 6,275,651 B1 | 8/2001 | Voit | |
| 6,278,840 B1 | 8/2001 | Basaganas Millan | |
| 6,285,830 B1 | 9/2001 | Basaganas Millan | |
| 6,289,176 B1 | 9/2001 | Martter et al. | |
| 6,302,559 B1 | 10/2001 | Warren | |
| 6,315,959 B1 | 11/2001 | Mandish | |
| 6,328,791 B1 | 12/2001 | Pillion et al. | |
| 6,342,676 B1 | 1/2002 | Ha | |
| 6,349,168 B1 | 2/2002 | Jaworski | |
| 6,352,210 B1 | 3/2002 | Requejo | |
| 6,354,513 B1 | 3/2002 | Basaganas Millan | |
| 6,361,752 B1 | 3/2002 | Demarest et al. | |
| 6,364,673 B1 | 4/2002 | Lee | |
| 6,368,564 B1 | 4/2002 | Smith | |
| 6,371,815 B1 | 4/2002 | Wetzel et al. | |
| 6,374,044 B1 | 4/2002 | Freidel | |
| 6,374,045 B1 | 4/2002 | Basaganas Millan | |
| 6,381,408 B1 | 4/2002 | Jaworski et al. | |
| 6,478,440 B1 * | 11/2002 | Jaworski et al. | 362/96 |
| 6,603,924 B1 | 8/2003 | Brown et al. | |
| 6,714,725 B1 | 3/2004 | Grone et al. | |
| 2001/0031225 A1 | 10/2001 | Mandish | |
| 2001/0053283 A1 | 12/2001 | Levine et al. | |
| 2002/0144992 A1 | 10/2002 | Vieira | |
| 2003/0138241 A1 | 7/2003 | Ambrosi et al. | |

FOREIGN PATENT DOCUMENTS

| | | | |
|---|---|---|---|
| DE | 41 31 613 | 3/1993 | |
| EP | 278653 A2 * | 8/1988 | 422/124 |
| EP | 0 296 807 | 12/1988 | |
| EP | 0 669 137 | 3/1995 | |
| EP | 0 911 041 | 4/1999 | |
| GB | 402507 | 12/1933 | |
| GB | 2 356 815 | 6/2001 | |
| WO | WO 00 76292 | 12/2000 | |
| WO | WO 01 10739 | 2/2001 | |
| WO | WO 01/68154 | 9/2001 | |
| WO | WO 01/93919 | 12/2001 | |

OTHER PUBLICATIONS

PCT International Search Report issued Apr. 21, 2004 for International Application No. PCT/US03/26754, International Filing Date Aug. 28, 2003, 4 pages.

PCT International Search Report issued Nov. 12, 2003 for International Application No. PCT/US03/25245, International Filing Date Aug. 13, 2003, 4 pages.

PCT International Search Report issued Oct. 7, 2003 for International Application No. PCT/US03/04082, International Filing Date Feb. 12, 2003, 8 pages.

PCT International Search Report issued Dec. 16, 2003 for International Application No. PCT/US03/25244, International Filing Date Aug. 13, 2003, 3 pages.

PCT International Search Report issued Dec. 16, 2003 for International Application No. PCT/US03/25246, International Filing Date Aug. 13, 2003, 3 pages.

PCT International Search Report issued Dec. 19, 2003 for International Application No. PCT/US03/25243, International Filing Date Aug. 13, 2003, 4 pages.

Brochure—"Decora Devices," by Leviton, date unknown, Section A, pp. A1-A36.

* cited by examiner

INTERMEDIARY DEVICE

CROSS-REFERENCE TO RELATED APPLICATIONS

This application claims priority to U.S. Provisional Application Ser. No. 60/407,394 entitled Intermediary Device and filed on Aug. 30, 2002 which is incorporated herein by reference.

TECHNICAL FIELD

This invention relates, generally, to a device which can serve as an intermediary device between other devices, and more particularly, to an intermediary device which alters the environment while leaving the other devices generally unaffected.

SUMMARY OF THE INVENTION

While the way in which the present invention addresses the disadvantages of the prior art will be discussed in greater detail below, in general, the present invention provides an intermediary device which attaches to and/or integrates with at least one other device, the intermediary device, altering a surrounding environment with little to no effect on devices to which it is attached.

BRIEF DESCRIPTION OF THE DRAWINGS

The subject invention will hereinafter be described in conjunction with the appended drawing figures, wherein like numerals denote like elements, and.

DETAILED DESCRIPTION

The following description is of exemplary embodiments of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth herein. For example, in the context of the present invention, the method and apparatus hereof find particular use in connection with environment altering systems such as air fresheners. However, generally speaking, various volatizable materials such as insect repellants, deodorizers, sanitizers, and/or the like are suitable for use in accordance with the present invention. Additionally, various embodiments of the present invention are described in conjunction with specific appliances and devices, though it should be appreciated that the scope of the present invention should not be considered limited to those specifically mentioned herein.

An intermediary device 100 in accordance with the present invention is provided for herein. Generally, device 100 comprises a structure configured to alter a surrounding environment, which can also be attached and/or integrated with at least one other device. For example, as mentioned above, device 100 may comprise an air freshener such as a solid, gel, liquid (e.g., scented oil) air freshening device which is attached to, for example and as described in further detail below, a home appliance.

Figure 1:
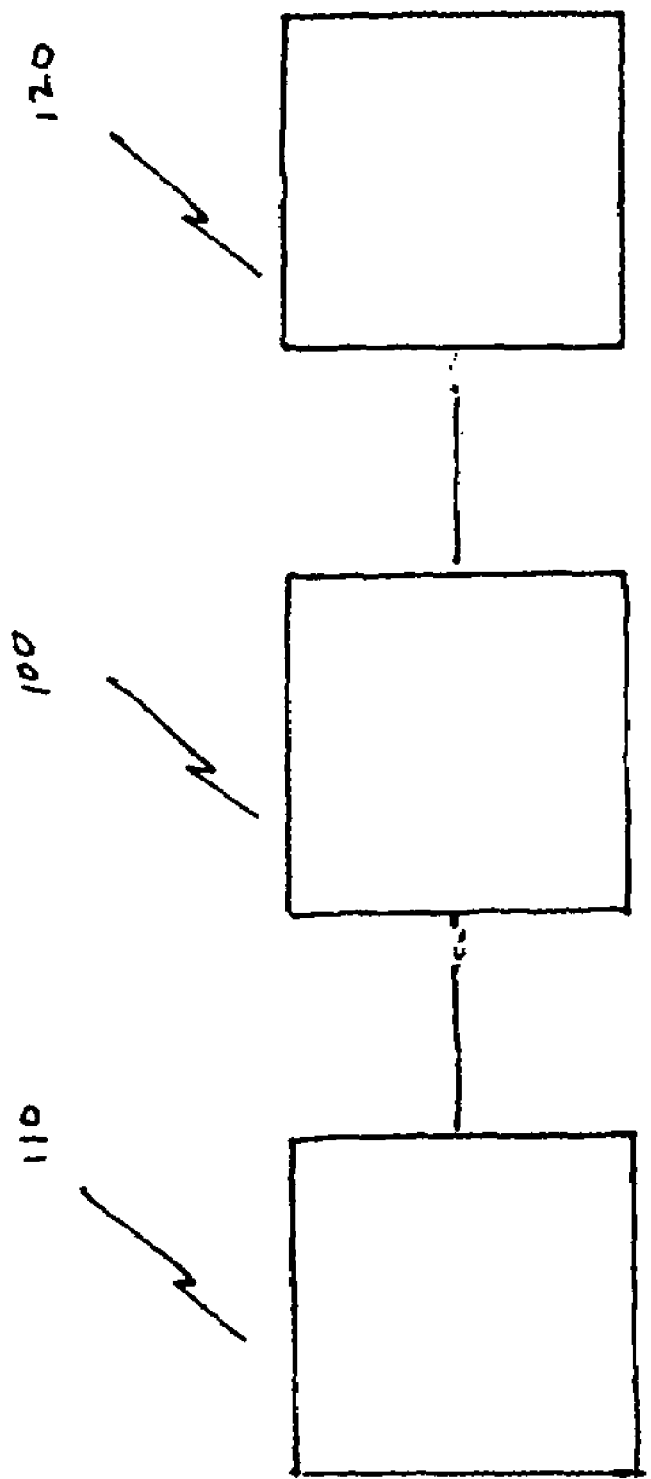
FIG. 1 is a block diagram illustrating an exemplary configuration of an intermediary device in accordance with an exemplary embodiment of the present invention.

In general, in accordance with various embodiments of the present invention, FIG. 1 is a block diagram of an exemplary intermediate vapor-dispensing device 100 configured to attach to a first device 110 and a second device 120. For example, in one exemplary embodiment, first device 110 is an electrical receptacle and second device 120 is a device which, in the absence of intermediary device 100, is typically plugged into the electrical receptacle.

Figure 2:
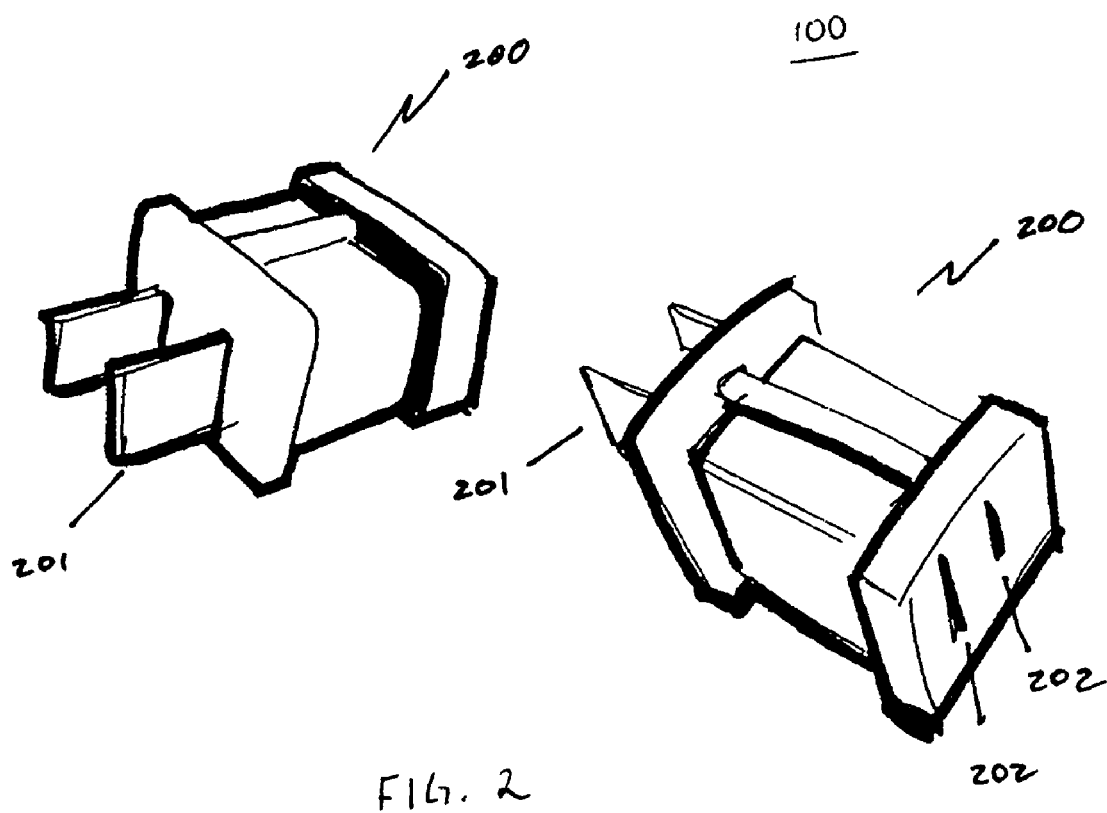
FIG. 2 are front and rear perspective views of an exemplary embodiment of an intermediary device in accordance with the present invention.
Figure 3:
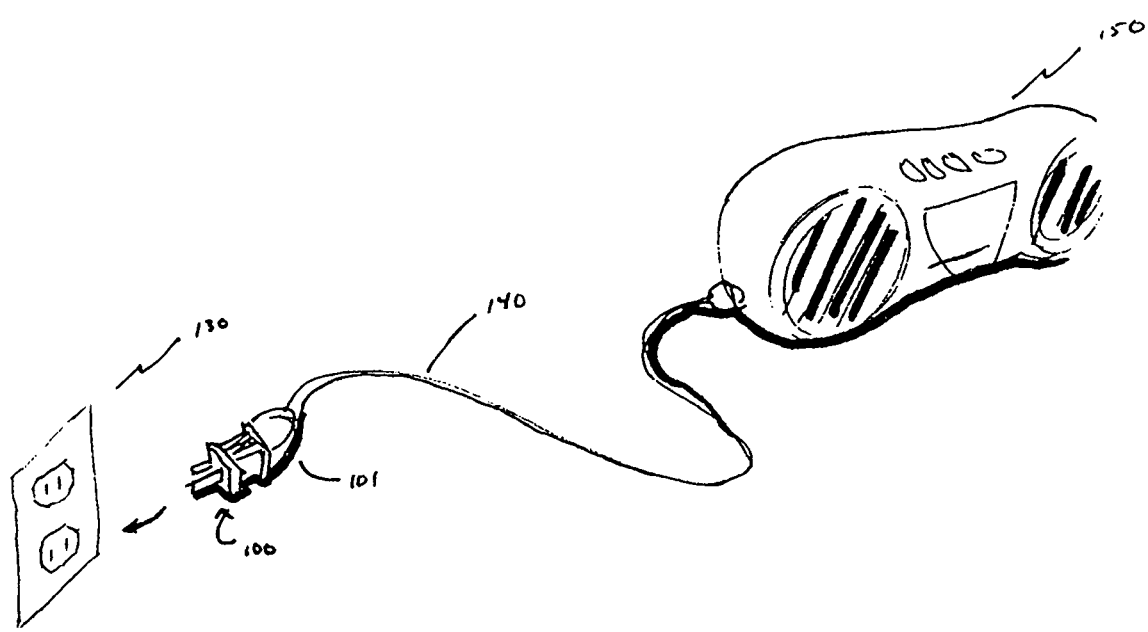
FIG. 3 is perspective view of the intermediary device of FIG. 2 in an exemplary environment.
Figure 4:
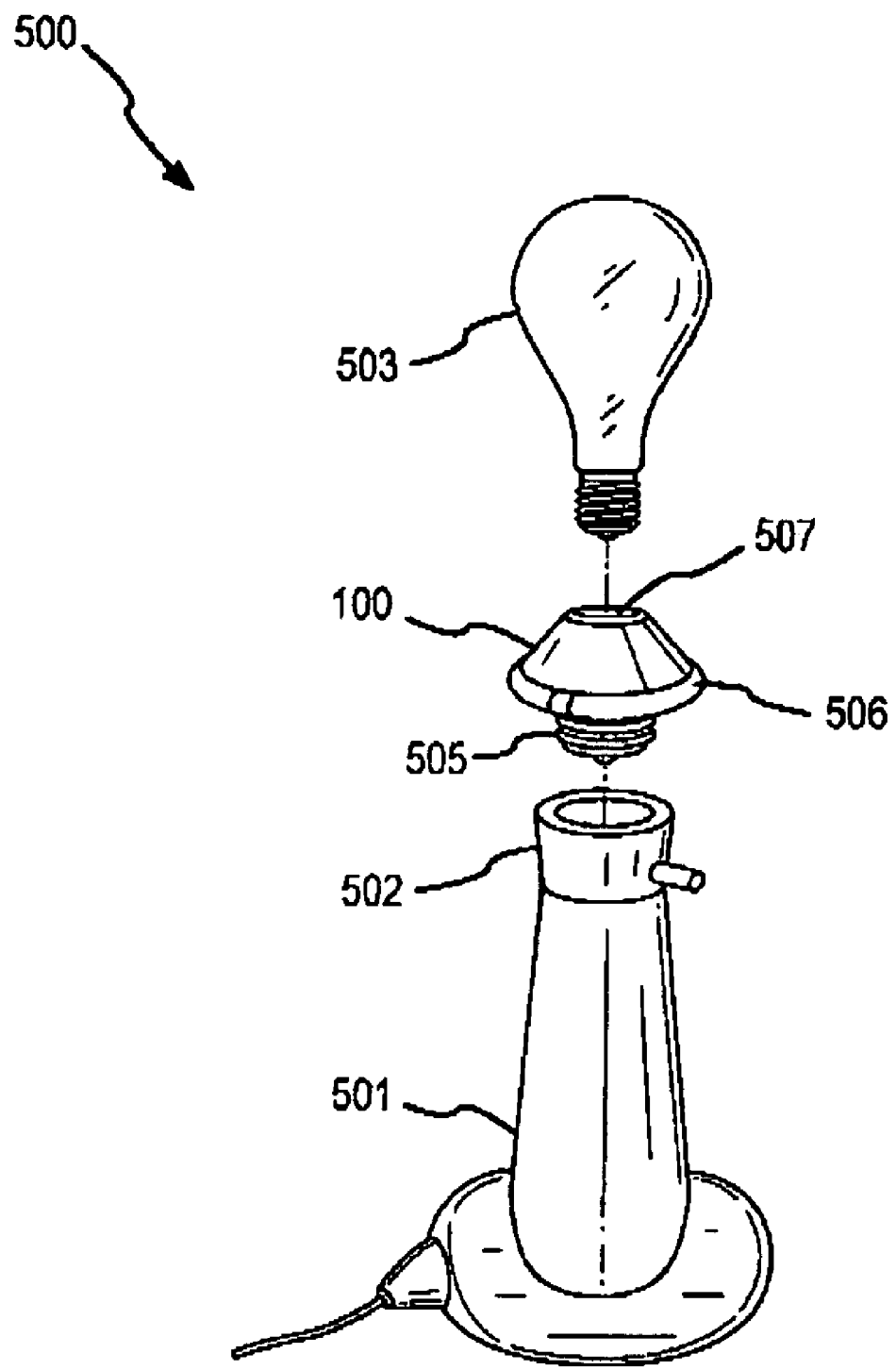
FIG. 4 is perspective view of another exemplary embodiment of an intermediary device the present invention.
Figure 5:
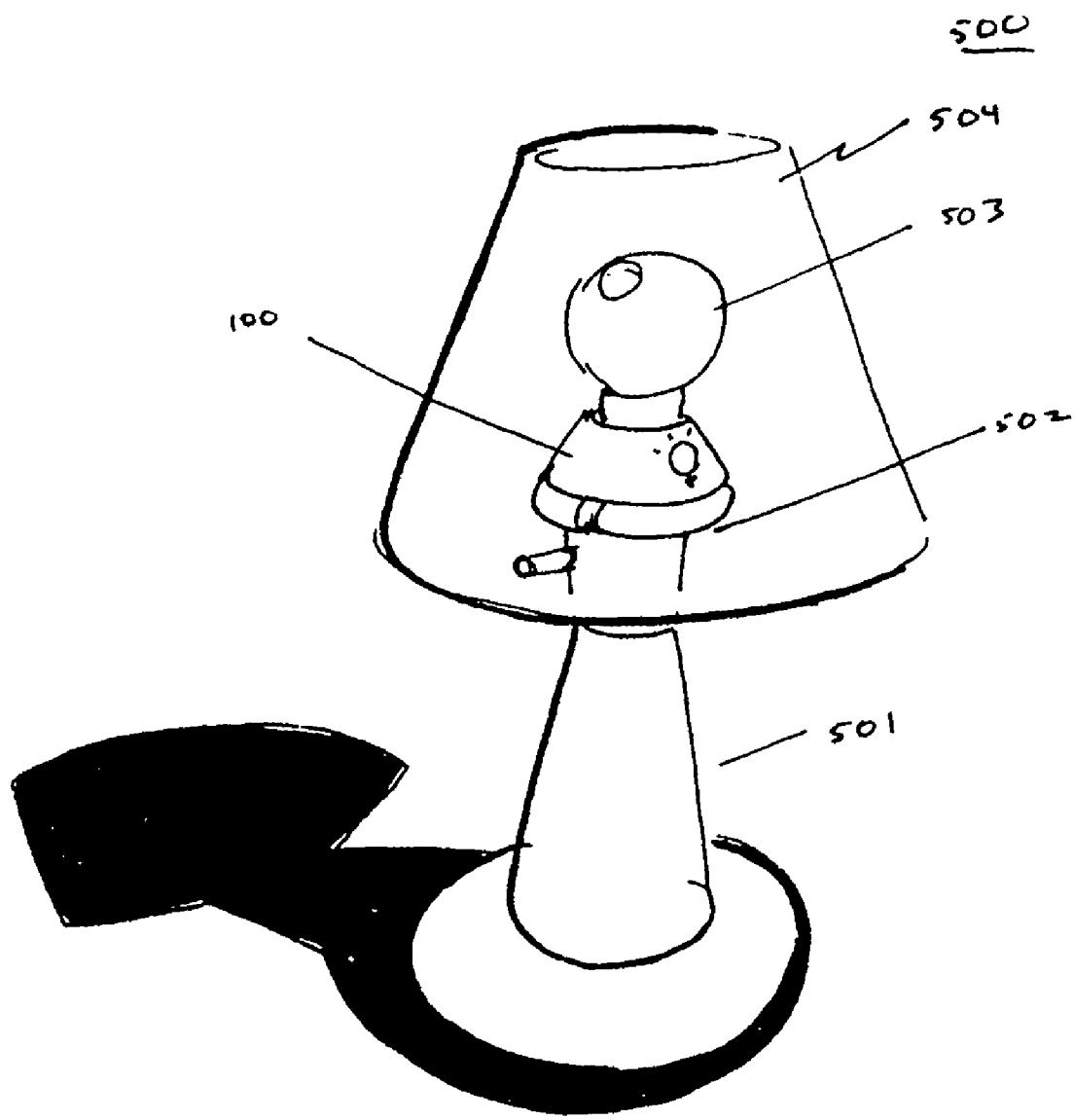
FIG. 5 is perspective view showing an alternative aspect of the exemplary embodiment of FIG. 4.
Figure 6:
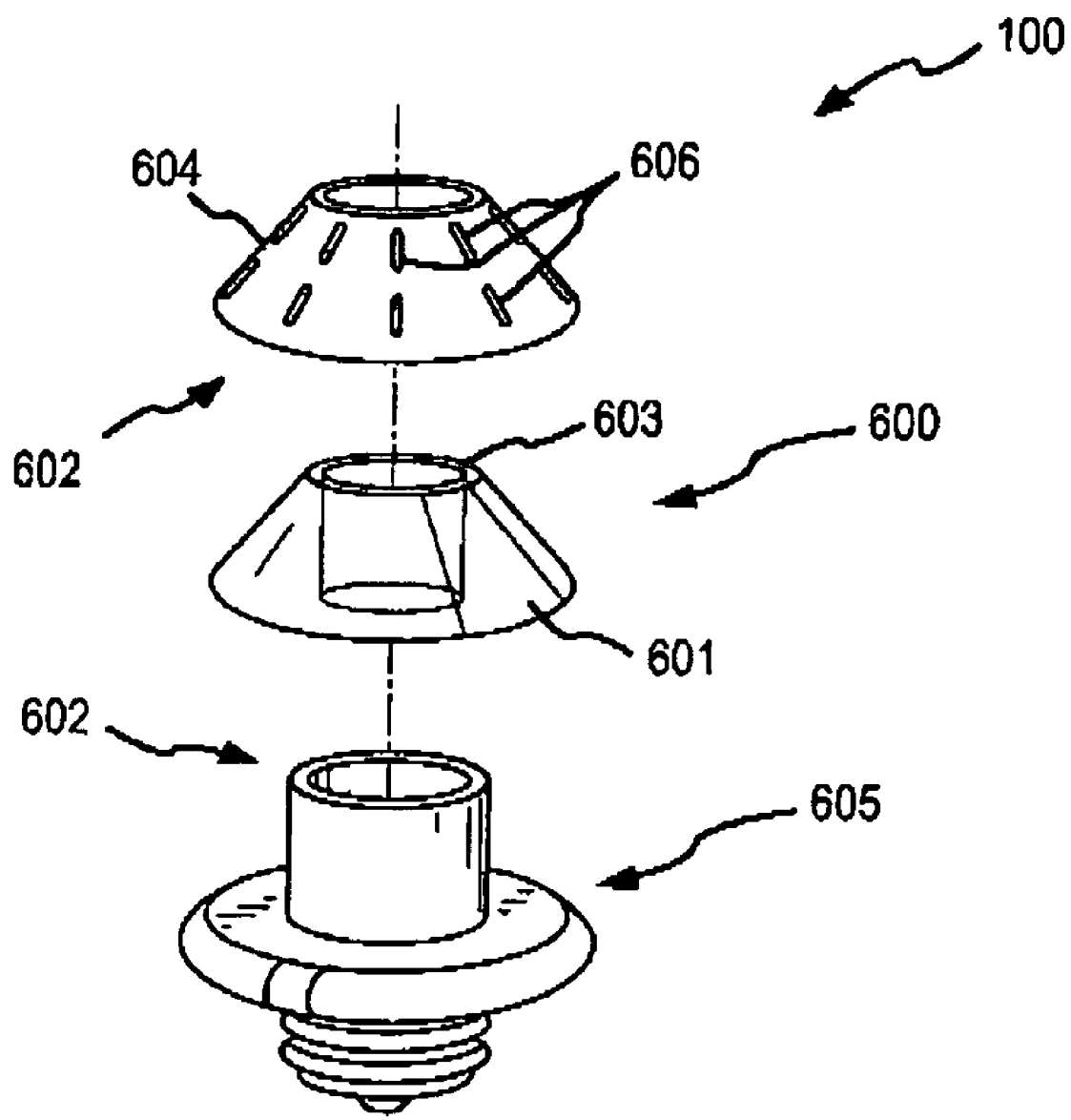
FIG. 6 is close-up perspective view an exemplary embodiment of the present invention.

For example, referring to the exemplary embodiments illustrated in FIGS. 2 and 3, and as described in further detail below, device 100 is configured to be positioned between a wall outlet 130 and an electrical cord 140 of an appliance (e.g., a radio as pictured) 150. Similarly, as shown in FIGS. 4–6, intermediary device 100 is integrated with a lamp 500 between a first device comprising a lamp socket 502 and a second device comprising a light bulb 503 which otherwise would be inserted into lamp socket 502. Thus, it should be apparent that, in its various embodiments, intermediate vapor-dispensing device 100 comprises any device configured to attach to a first device 110 and a second device 120 having various properties described herein below.

In accordance with various embodiments of the present invention, device 100 is a discrete, low-noticeability unit. In this context, "discrete, low-noticeability" refers generally to various characteristics of the same. For example, in the context of an intermediary device which is located between a wall outlet and a standard plug (e.g., connected to radio, alarm clock, etc.), as can be seen in FIGS. 2 and 3, intermediary device 100 is generally about the size and shape of a standard plug base 101. For example, a body 200 of intermediary device 100 can be described by length L and width W, (e.g. if rectangular) or diameter D (e.g. if cylindrical), and for intermediary device 100 to generally mimic the appearance of the plug on a conventional electrical cord for example, the ratio of length L to width W (or to diameter D) is preferably from about 1:1 to about 2:1. Most preferably, and in order to more closely mimic the appearance of the plug on a conventional electrical cord, the ratio of L/W or L/D should be about 1.25:1 to about 1.75:1. In such embodiments, on one end of body 200, electrical outlet prongs 201 are provided for insertion into an electrical receptacle. In the illustrated embodiment, prongs 201 are configured for a standard two-prong outlet, though any configuration (three-prong, grounded outlet, European style, 220 amp, etc.) may likewise be used. On an opposing end of base 200, intermediary device outlets 202 are provided for insertion of other devices. Again, in the illustrated embodiment, outlets 202 are configured in a standard two-prong configuration, though any configuration may likewise be used, and, in fact, may desired in instances where intermediary device 100 is used as an adapter for plugging components into receptacles which otherwise might not fit (e.g., where a wall outlet is a two-prong configuration and an appliance is a three-prong configuration, prongs 201 may be two-prong, while outlets 202 may be three-prong). Thus, intermediary device 100 is at least partially "camouflaged" in that it suitably blends in with base 101 of the plug of appliance 150.

However, discrete and/or low-noticeability may also be obtained in a number of alternative manners. For example, with momentary reference to FIG. 5, in the context of a lamp 500 comprising, generally, a lamp base 501, a socket 502 and a light bulb 503, intermediary device 100 may be disguised by the placement of a lamp shade 504 or other hiding feature which covers and/or obstructs the viewing of intermediary device 100.

Of course, in addition to separate hiding features, intermediary device 100 may also have other generally discrete/camouflaged characteristics as in the case of the wall plug and other embodiments. For example, with reference to FIGS. 4–6, in the lamp embodiment, intermediary device 100 comprises a shape which has a natural contour corresponding to the shape of the lamp.

In various embodiments, intermediary device 100 comprises materials suitable for use in applications where electricity or heat are present. For example, intermediary device 100 may comprise a base material of a non-conductive nature such as plastic, ceramic, fiberglass or the like. Intermediary device 100 may further comprise various conductive materials (e.g., copper, aluminum, other metals or the like), such that electric current or heat can pass through intermediary device 100.

In an embodiment such as that described in FIGS. 4–6, intermediary device 100 has a male end 505 configured for insertion into socket 502. In many instances, male end 505 will thus be threaded for insertion and fastening into socket 502. However, various alternative methods for insertion/fastening now known or as yet unknown are likewise contemplated herein.

Male end 505 is attached to or otherwise integrated with an environment altering portion 506. In this embodiment, environment altering portion 506 comprises various components and structure which serve to alter the environment surrounding intermediary device 100. For example, in the context of a vapor-dispensing device 100, portion 506 comprises any combination of a material to be vaporized (insect repellant, air freshener, deodorizer or the like) in various forms (gel, solid, liquid, etc.), heating elements, material evacuation elements (e.g., a fan), control switches, switches for activating and de-activating the environment altering device and/or devices to which intermediary device 100 is connected, venting and the like. Of course, it should be appreciated that in various embodiments, some of these components may not be present, and other components not listed here may be present. Nonetheless, all of the same variously fall within the scope of the present invention.

In this exemplary embodiment, intermediary device 100 further comprises a female end 507. Female end 507 comprises a socket for receiving light bulb 503. Generally, the socket of female end 507 is configured to receive and retain light bulb 503, and thus, in instances where light bulb 503 is threaded, female end 507 will be similarly sized and threaded. In alternative embodiments, female end 507 may be configured in non-threaded manners yet which retain light bulb 503, such as, for example, by snap fit. Similarly, intermediary device 100 and/or female end 507 may act in an adaptive sense in that the size of female end 507 may not correspond to socket 502 so as to allow various light bulbs which would not otherwise fit socket 502 to be used with lamp 500.

Briefly, however, in other embodiments, intermediary device 100 need not follow such contours or have male and female ends, but rather may comprise a configuration which is separate from the typical plug and socket type configurations described above. For example, intermediary device 100 may comprise, in various embodiments a configuration which encompasses part of first or second device 110, 120. One such example might include a "ring" configuration which encircles and connects with lamp socket 502, but is not configured with its own socket 507 and rather, bulb 503 still connects with socket 502.

As mentioned above, intermediary device 100 comprises various elements which alter the environment surrounding device 100. One such example is alteration by dispensation of a vapor. In such embodiments, in addition to male and female ends (505, 507) and generally within altering portion 506, with reference to FIG. 6, intermediary device 100 comprises a reservoir 600 for containing a material to be dispensed 601 and a retainer 602 configured for holding reservoir 600.

Briefly, retainer 602 is any mechanism/structure capable of receiving and retaining reservoir 600. For example, the embodiment of FIG. 6 depicts retainer 602 as a two-piece structure which holds reservoir 600. In various embodiments, reservoir 600 has a predetermined shape; in this example, frusto-conical with a hollow core 603 (e.g., to fit around male end 505). Retainer 602 comprises an upper portion 604 and a lower portion 605. Upper portion 604 has a similar shape as reservoir 600 so that upper portion 604 can encompass reservoir 600 and secure to lower portion 605, thereby retaining reservoir 600. Briefly, in accordance wit various aspects of the present invention, various sections of intermediary device 100 may comprise features which facilitate intermediary devices altering the environment, such as, for example and as illustrated in FIG. 6, vents 606.

Finally, while the present invention has been described above with reference to various exemplary embodiments, many changes, combinations and modifications may be made to the exemplary embodiments without departing from the scope of the present invention. For example, the various components may be implemented in alternate ways. These alternatives can be suitably selected depending upon the particular application or in consideration of any number of factors associated with the operation of the system. In addition, the techniques described herein may be extended or modified for use with other types of devices. These and other changes or modifications are intended to be included within the scope of the present invention.

What is claimed is:

1. An intermediary device comprising,
    a vaporizing device for volatilizing a vapor producing material having a first male end configured with light bulb threads and a second female end configured with light socket threads for receipt of a light bulb, said vaporizing device having a heat conduit to convey heat from said light bulb to said vapor producing material to boost volatilization; and
    an electrical connection between said first end and said second end.

2. The intermediary device of claim 1, wherein said vapor producing material comprises at least one of a fragrance, deodorizer, sanitizer and insecticide vapor producing material.

3. The intermediary device of claim 1, wherein said vaporizing device is electrically powered by screwing said first end into a light bulb socket.

4. The intermediary device of claim 1, wherein said vaporizing device further comprises an electrical connection between said first end and a resistive heating element to heat said vapor producing material.

5. The intermediary device of claim 1, wherein said vaporizing device comprises a reservoir to hold said vapor producing material and a vented heating element.

* * * * *